(12) United States Patent  
Stone et al.

(10) Patent No.: US 8,236,059 B2
(45) Date of Patent: Aug. 7, 2012

(54) SHOULDER PROTHESIS

(75) Inventors: Kevin T. Stone, Winona Lake, IN (US); Nicholas M. Cordaro, Oceanside, CA (US)

(73) Assignee: Biomet Manufacturing, Inc., Warsaw, IN (US)

( * ) Notice: Subject to any disclaimer, the term of this patent is extended or adjusted under 35 U.S.C. 154(b) by 0 days.

(21) Appl. No.: 12/911,238

(22) Filed: Oct. 25, 2010

(65) Prior Publication Data

US 2011/0035015 A1 Feb. 10, 2011

Related U.S. Application Data

(62) Division of application No. 11/120,111, filed on May 2, 2005, now Pat. No. 7,819,923, which is a division of application No. 10/192,787, filed on Jul. 10, 2002, now Pat. No. 6,942,699.

(60) Provisional application No. 60/304,651, filed on Jul. 11, 2001.

(51) Int. Cl.
*A61F 2/40* (2006.01)

(52) U.S. Cl. ................................ 623/19.14

(58) Field of Classification Search .... 623/19.11–19.14, 623/20.14, 22.11, 22.4, 22.43, 23.15
See application file for complete search history.

(56) References Cited

U.S. PATENT DOCUMENTS

| | | | |
|---|---|---|---|
| 3,815,157 A | 6/1974 | Skorecki et al. | |
| 3,842,442 A | 10/1974 | Kolbel et al. | |
| 3,916,451 A | 11/1975 | Buechel et al. | |
| 3,978,528 A | 9/1976 | Crep | |
| 3,979,778 A | 9/1976 | Stroot | |
| 4,003,095 A | 1/1977 | Gristina | |
| 4,030,143 A | 6/1977 | Elloy et al. | |
| 4,040,131 A | 8/1977 | Gristina | |
| 4,135,517 A | 1/1979 | Reale | |
| 4,179,758 A | 12/1979 | Gristina | |
| 4,206,517 A | 6/1980 | Pappas et al. | |
| 4,693,723 A | 9/1987 | Gabard et al. | |
| 4,822,370 A | 4/1989 | Schelhas et al. | |
| 4,865,605 A | 9/1989 | Dines et al. | |

(Continued)

FOREIGN PATENT DOCUMENTS

DK 19509037 9/1996

(Continued)

OTHER PUBLICATIONS

'Buechel-Pappas.TM. Total Shoulder System', Endotec, Jul. 1991.

(Continued)

*Primary Examiner* — Alvin J Stewart
(74) *Attorney, Agent, or Firm* — Harness, Dickey

(57) ABSTRACT

The present teachings are directed to a modular shoulder prosthesis having an adjustable radial offset and/or angular inclination provided by relative rotation of an adapter interdisposed between the stem and the head. In one example, a shoulder prosthesis comprises a stem having a first longitudinal axis. The shoulder prosthesis can also include an adaptor including a first taper. The first taper can have a first taper axis. The shoulder prosthesis can include a head rotatably supported by the adaptor. The head can have a semi-spherical articulating surface. The head can be coupled to the first taper and can be positionable relative to the stem through rotation of the adaptor about the first taper axis for adjusting an offset of the head relative to the longitudinal axis of the stem.

12 Claims, 7 Drawing Sheets

U.S. PATENT DOCUMENTS

| | | | |
|---|---|---|---|
| 4,865,609 A | 9/1989 | Roche | |
| 4,919,670 A | 4/1990 | Dale et al. | |
| 4,957,510 A | 9/1990 | Cremascoli et al. | |
| 4,963,155 A | 10/1990 | Lazzeri et al. | |
| 5,080,673 A | 1/1992 | Burkhead et al. | |
| 5,080,685 A | 1/1992 | Bolesky et al. | |
| 5,135,529 A | 8/1992 | Paxson et al. | |
| 5,181,928 A | 1/1993 | Bolesky et al. | |
| 5,201,882 A | 4/1993 | Paxson | |
| 5,222,984 A | 6/1993 | Forte | |
| 5,314,479 A | 5/1994 | Rockwood, Jr. et al. | |
| 5,358,526 A | 10/1994 | Tornier et al. | |
| 5,462,563 A | 10/1995 | Shearer et al. | |
| 5,507,817 A | 4/1996 | Craig et al. | |
| 5,507,818 A | 4/1996 | McLaughlin | |
| 5,507,824 A | 4/1996 | Lennox | |
| 5,549,682 A | 8/1996 | Roy | |
| 5,580,352 A | 12/1996 | Sekel | |
| 5,702,457 A | 12/1997 | Walch et al. | |
| 5,702,486 A | 12/1997 | Craig et al. | |
| 5,723,018 A | 3/1998 | Cyprien et al. | |
| 5,728,161 A | 3/1998 | Camino et al. | |
| 5,902,340 A | 5/1999 | White et al. | |
| 5,910,171 A | 6/1999 | Kummer et al. | |
| 5,961,555 A | 10/1999 | Huebner | |
| 6,033,439 A | 3/2000 | Camino et al. | |
| 6,045,582 A | 4/2000 | Prybyla | |
| 6,102,953 A | 8/2000 | Huebner | |
| 6,129,764 A | 10/2000 | Servidio | |
| 6,171,341 B1 | 1/2001 | Boileau et al. | |
| 6,197,062 B1* | 3/2001 | Fenlin | 623/19.12 |
| 6,197,063 B1 | 3/2001 | Dews et al. | |
| 6,206,925 B1 | 3/2001 | Tornier et al. | |
| 6,228,120 B1 | 5/2001 | Leonard et al. | |
| 6,364,910 B1 | 4/2002 | Shultz et al. | |
| 6,368,352 B1 | 4/2002 | Camino et al. | |
| 6,620,197 B2 | 9/2003 | Maroney et al. | |
| 6,626,946 B1 | 9/2003 | Walch et al. | |
| 6,719,799 B1* | 4/2004 | Kropf | 623/19.14 |
| 6,761,740 B2 | 7/2004 | Tornier et al. | |
| 6,790,234 B1 | 9/2004 | Frankle | |
| 6,890,358 B2 | 5/2005 | Ball et al. | |
| 6,942,699 B2* | 9/2005 | Stone et al. | 623/19.14 |
| 6,974,483 B2* | 12/2005 | Murray | 623/22.42 |
| 6,986,790 B2 | 1/2006 | Ball et al. | |
| 7,022,141 B2* | 4/2006 | Dwyer et al. | 623/22.12 |
| 7,097,663 B1 | 8/2006 | Nicol et al. | |
| 7,135,044 B2 | 11/2006 | Bassik et al. | |
| 7,175,663 B1 | 2/2007 | Stone | |
| 7,189,261 B2* | 3/2007 | Dews et al. | 623/19.14 |
| 7,238,207 B2* | 7/2007 | Blatter et al. | 623/19.14 |
| 7,621,961 B2 | 11/2009 | Stone | |
| 7,819,923 B2* | 10/2010 | Stone et al. | 623/19.14 |
| 2001/0049561 A1 | 12/2001 | Dews et al. | |
| 2001/0053935 A1* | 12/2001 | Hartdegen et al. | 623/19.12 |
| 2002/0120339 A1 | 8/2002 | Callaway et al. | |
| 2002/0138148 A1 | 9/2002 | Hyde | |
| 2002/0156534 A1* | 10/2002 | Grusin et al. | 623/19.14 |
| 2003/0028253 A1* | 2/2003 | Stone et al. | 623/19.14 |
| 2003/0097183 A1 | 5/2003 | Rauscher et al. | |
| 2003/0114933 A1 | 6/2003 | Bouttens et al. | |
| 2003/0158605 A1 | 8/2003 | Tornier | |
| 2004/0064189 A1 | 4/2004 | Maroney et al. | |
| 2004/0064190 A1 | 4/2004 | Ball et al. | |
| 2004/0220673 A1 | 11/2004 | Pria | |
| 2004/0220674 A1 | 11/2004 | Pria | |
| 2006/0020344 A1 | 1/2006 | Shultz et al. | |
| 2007/0198094 A1* | 8/2007 | Berelsman et al. | 623/19.14 |
| 2009/0192621 A1 | 7/2009 | Winslow et al. | |
| 2009/0210065 A1* | 8/2009 | Nerot et al. | 623/19.14 |
| 2009/0270993 A1* | 10/2009 | Maisonneuve et al. | 623/19.14 |
| 2011/0035013 A1* | 2/2011 | Winslow et al. | 623/19.13 |
| 2011/0035015 A1* | 2/2011 | Stone et al. | 623/19.14 |
| 2011/0054624 A1* | 3/2011 | Iannotti | 623/19.14 |
| 2011/0118846 A1* | 5/2011 | Katrana et al. | 623/19.13 |

FOREIGN PATENT DOCUMENTS

| | | |
|---|---|---|
| EP | 0257359 | 3/1988 |
| EP | 0599429 | 6/1994 |
| EP | 0664108 | 7/1995 |
| EP | 0679375 | 11/1995 |
| EP | 0712617 | 5/1996 |
| EP | 0797964 | 10/1997 |
| EP | 1472999 | 11/2004 |
| EP | 1520560 | 4/2005 |
| EP | 1639965 | 3/2006 |
| FR | 2574283 | 6/1986 |
| FR | 2652498 | 4/1991 |
| FR | 2664809 | 1/1992 |
| FR | 2704747 | 11/1994 |
| FR | 2721200 | 12/1995 |
| FR | 2848099 | 6/2004 |
| FR | 2852229 | 9/2004 |
| GB | 2405346 | 3/2005 |
| WO | 9522302 | 8/1995 |
| WO | 9617553 | 6/1996 |
| WO | 9846172 | 10/1998 |
| WO | 0015154 | 3/2000 |

OTHER PUBLICATIONS

Thabe et al., 'Die endoprothetische Versorgung des rheumatischen Schultergelenkes', Aktuelle Rheumatologie, vol. 19 (1994), pp. 155-160 (with English abstract).

Surgery Eases Rotator Cuff Pain' by Ruth Campbell Odessa American, online article, (2 sheets) dated Feb. 9, 2005.

The Delta CTAä Reverse Shoulder System, copyright Johnson & Johnson Gateway LLC 2000-2005 online article (2 sheets) dated Feb. 9, 2005.

European Search Report for EP06254735 mailed Apr. 5, 2007.

International Search Report for PCT/US02/22040 mailed Apr. 4, 2003.

Final Office Action for U.S. Appl. No. 11/234,743 Mailed Jun. 15, 2010.

Non-Final Office Action for U.S. Appl. No. 11/234,743 Mailed Dec. 2, 2009.

Non-Final Office Action for U.S. Appl.No. 11/234,743 Mailed Dec. 21, 2010.

Non-Final Office Action for U.S. Appl. No. 12/390,652 Mailed Feb. 28, 2011.

* cited by examiner

SHOULDER PROTHESIS

CROSS-REFERENCE TO RELATED APPLICATIONS

This application is a divisional of U.S. patent application Ser. No. 11/120,111, filed on May 2, 2005, which is a divisional of U.S. patent application Ser. No. 10/192,787, filed on Jul. 10, 2002, now U.S. Pat. No. 6,942,699, issued Sep. 13, 2005. U.S. patent application Ser. No. 10/192,787 claims the benefit of U.S. Provisional Application No. 60/304,651, filed Jul. 11, 2001. The disclosures of the above referenced applications are incorporated herein by reference.

BACKGROUND

The present teachings relate to a prosthesis for replacing and reconstructing a portion of the humerus and more specifically to a modular humeral prosthesis, which allows for total shoulder joint replacement.

The shoulder joint is considered to be one of the most complex joints in the body. The scapula, the clavicle and the humerus all meet at the shoulder joint. The head of the humerus fits into a shallow socket of the scapula called the glenoid fossa to form a mobile joint. When the joint is articulated, the humeral head moves in the glenoid fossa to provide a wide range of motion. The shoulder joint may suffer from various maladies including rheumatoid arthritis, osteoarthritis, rotator cuff arthropathy, a vascular necrosis, bone fracture or failure of previous joint implants. If severe joint damage occurs and no other means of treatment is found to be effective, then a total shoulder reconstruction may be necessary.

A shoulder joint prosthesis generally includes the replacement of the ball of the humerus and, optionally, the socket of the shoulder blade with specially designed artificial components. The bio-kinematics, and thus the range of motion in the shoulder vary greatly among prospective patients for reconstruction shoulder surgery. The humeral component typically has a metal shaft or stem with a body portion that is embedded in the resected humerus and a generally hemispherical head portion supported on the stem. The head slidingly engages a glenoid implant on the glenoid fossa. During reconstructive surgery, the components of the prosthesis are matched with the bio-kinematics of the patient in an effort to maintain the natural range of motion of a healthy shoulder joint. Thus, a shoulder prosthesis design must be readily adaptable to a wide range of bio-kinematics for prospective patients.

In this regard, shoulder prostheses are generally available as either unitary structures or modular components. With unitary shoulder prosthesis, a large inventory of differently sized prostheses must be maintained to accommodate the different bone sizes and joint configurations of the prospective patients. With such unitary shoulder prosthesis, the patient is typically evaluated by x-ray to determine the approximate prostheses size needed for reconstruction. A number of differently sized prostheses are selected as possible candidates based upon this preliminary evaluation. Final selection of the appropriately sized prosthesis is made during the surgery. With unitary shoulder prosthesis, each design represents a compromise that is unable to achieve all of the natural range of motion of a healthy shoulder joint because of the fixed geometric configuration in their design.

Modular prostheses systems which reduce the need to maintain large inventories of various sized components are well known in the art. Conventionally, the humeral prosthesis includes two components—a humeral stem component and a spherical head releasably coupled to the stem. Alternately, a three component design is known in which the stem and shoulder are interconnected with an adapter. In either of the two-piece or three-piece designs, a radial offset or angulator inclination of the head relative to the stem is provided in individual components. For example, in the three-piece design, an adapter may be configured with a fixed radial offset of 2 millimeters or an angular inclination of 5 degrees. Different radial offsets or angular inclinations are achieved through the use of different adapters or heads. In this regard, conventional modular shoulder prosthesis kits include multiple redundant components such as adapters and heads to achieve a range of prosthetic options. While providing an advantage over the unitary design in reducing the number of components needed, a rather large inventory of head components and/or adapter components must be maintained to provide the desired range of geometric configurations with the conventional modular shoulder prostheses. Therefore, there is a need for modular shoulder prostheses which are readily adaptable to provide a range of geometric configurations, i.e. radial offsets of angular inclination while minimizing the number of components required.

SUMMARY

In accordance with the present teachings, a modular joint prosthesis system is provided. Specifically, a humeral component for a total shoulder prosthesis includes an adapter and a head component which cooperate to provide a range of radial offsets and/or angular inclinations and which are adapted to be used in conjunction with a stem.

In one embodiment, a humeral component for a total shoulder prosthesis is provided for adjustable radial offset of the head with respect to the stem. The shoulder prosthesis includes an adapter interposed between a stem and a head. The adapter is eccentrically coupled to the stem such that relative angular positioning of the adapter on the stem will effect a first adjustment in the radial offset. Likewise, the head component is eccentrically coupled to the adapter as such that relative angular position of the head on the adapter will effect a second radial offset adjustment. By selectively positioning the adapter and the head component with respect to the stem, an infinite adjustment of the radial offset within a given range may be achieved. In one example, indicia are provided at the interface between the adapter and the head to indicate the offset vector (i.e., offset amount and direction).

In another embodiment, a humeral component for a total shoulder prosthesis is provided for adjustable angular inclination of the head component relative to the stem component. The shoulder prosthesis includes an adapter interposed between a stem and a head. The adapter is coupled to the stem in a first angled or non-orthogonal orientation such that relative rotational positioning of the adapter on the stem will effect a first adjustment in the direction of the angular inclination. Likewise, the adapter is coupled to the head in a second angled or non-orthogonal orientation as such that relative rotational position of the head on the adapter will effect a second adjustment in the direction of the angular inclination. By selectively positioning the adapter and the head component with respect to the stem, an infinite adjustment of the angular inclination within a given range may be achieved.

In yet another embodiment, the present teachings include an adapter interposed between a stem and a head. The adapter includes a ball stud having a shank coupled to the stem and a ring coupled to the head. The ring has a spherical bearing surface which cooperates with a ball portion of the ball stud such that an angular adjusted between the ball stud and the ring may be effected. The ring is eccentrically coupled to the head such that relative angular positioning of the ring in the head will effect an adjustment in the radial offset.

The joint prosthesis system of the present teachings provides great flexibility in the adjustment of important biokinematic parameters for the prosthesis systems while minimizing the number of components required for the modular system.

Also provided according to the present teachings is a shoulder prosthesis comprising a stem having a first longitudinal axis. The shoulder prosthesis can also include an adaptor including a first taper. The first taper can have a first taper axis. The shoulder prosthesis can also include a plurality of indicia. The shoulder prosthesis can include a head rotatably supported by the adaptor. The head can have a semi-spherical articulating surface. The head can be coupled to the first taper and can be positionable relative to the stem through rotation of the adaptor about the first taper axis for adjusting a radial offset of the head relative to the longitudinal axis of the stem. The plurality of indicia can indicate an alignment of the radial offset.

Further provided is a shoulder prosthesis comprising a stem having a longitudinal axis and a proximal face. The proximal face can define a bore. The shoulder prosthesis can include an adaptor having a first portion coupled to a second portion. At least a portion of the first portion can be received within the bore of the stem to couple the adaptor to the stem. The first portion can also have a first diameter. The second portion can have a second diameter different than the first diameter, and can define a first taper. The adaptor can also include a plurality of indicia. The shoulder prosthesis can include a head having a bottom face opposite a semispherical articulating surface. The bottom face can have a second taper that mates with the first taper of the second portion to couple the head to the adaptor. The rotation of the adaptor relative to the stem can adjust the radial offset of the head relative to the longitudinal axis of the stem. The plurality of indicia on the adaptor can indicate an alignment of the radial offset.

According to the present teachings, provided is a shoulder prosthesis comprising a stem having a longitudinal axis and a proximal face. The proximal face can define a bore. The shoulder prosthesis can include an adaptor having a first portion opposite a second portion. At least a portion of the first portion can be received within the bore of the stem to couple the adaptor to the stem. The first portion can have a first diameter and can be positioned about a first axis. The second portion can have a second diameter smaller than the first diameter. The second portion can define a first taper and can be positioned about a second axis. The second axis can be offset from the first axis. The adaptor can also include a plurality of indicia. The shoulder prosthesis can also include a head having a semispherical articulating surface and a bottom face opposite the semispherical articulating surface. The head can also include a third axis, which can be offset from the first axis and the second axis. The bottom face can have a second taper that mates with the first taper of the second portion to couple the head to the adaptor. The rotation of the adaptor relative to the stem can adjust the radial offset of the head relative to the longitudinal axis of the stem. The plurality of indicia on the adaptor can indicate an alignment of the radial offset.

Further areas of applicability will become apparent from the description provided herein. It should be understood that the description and specific examples are intended for purposes of illustration only and are not intended to limit the scope of the present teachings.

BRIEF DESCRIPTION OF THE DRAWINGS

The drawings described herein are for illustration purposes only and are not intended to limit the scope of the present teachings in any way.

DETAILED DESCRIPTION

Figure 1:
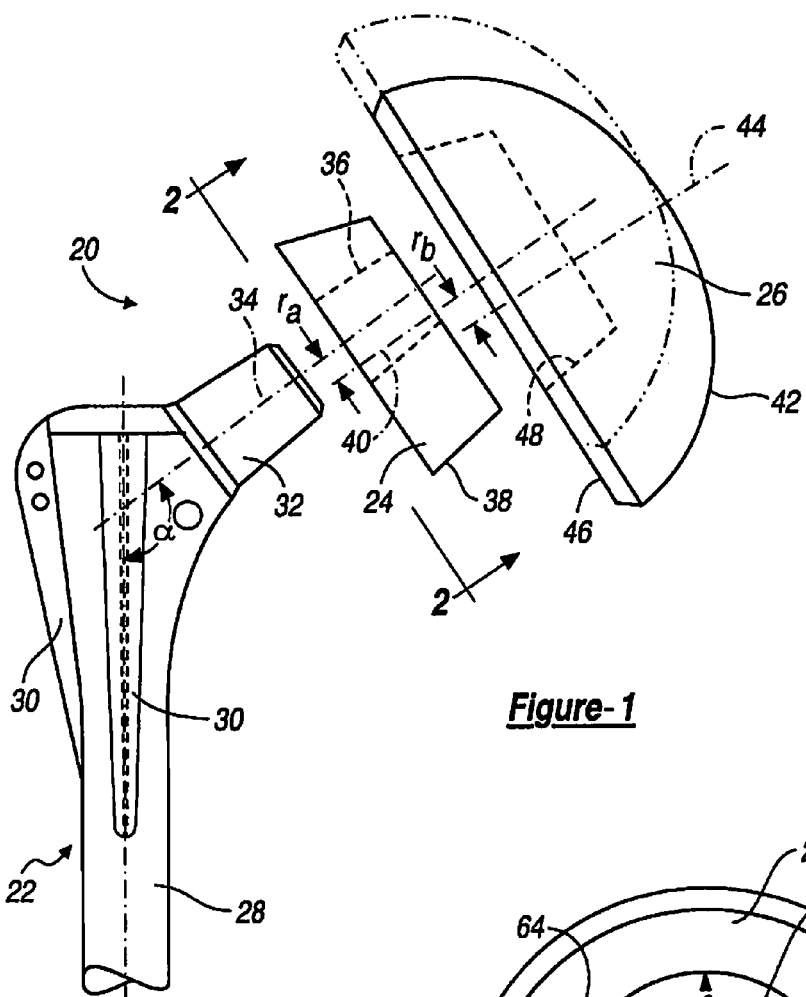
FIG. 1 is an exploded front view of a modular shoulder prosthesis system in accordance with the present teachings.

The following description is merely exemplary in nature and is not intended to limit the present teachings, application, or uses. It should be understood that throughout the drawings, corresponding reference numerals indicate like or corresponding parts and features. Although the following description is related generally to a modular joint prosthesis system which provides adjustment of the radial offset and/or angular inclination of the head relative to the stem, it will be understood that the system as described and claimed herein can be used in any appropriate surgical procedure. Thus, it will be understood that the following discussions are not intended to limit the scope of the present teachings and claims herein.

With reference now to FIG. 1, shoulder prosthesis 20 in accordance with the present teachings is illustrated to include a stem 22, an adapter 24 and a head 26. Stem 22 includes a rod portion 28 adapted to be received in the medullary canal of the humerus. A plurality of fins 30 are formed near the upper end of rod 28 for locating and fixing the stem within a humerus. A male taper 32 extends obtusely from rod 28 to provide a location for interconnecting stem 22 with adapter 24. Male taper 32 extends from stem 22 along axis 34. Stem 22 is of the type manufactured and sold by Biomet, Inc. as a component in its Bi-Angular® Shoulder System.

Adapter 24 is a generally cylindrical disc having a female taper 36 formed therein for receiving male taper 32 of stem 22. The outer surface 38 of adapter 24 defines a male taper. Female taper 36 is eccentrically located in adapter 24 such that central axis 34 of female taper 36 is not collinear with central axis 40 of adapter 24. Instead, central axis 40 is radially offset from central axis 34 by an amount indicated as $r_a$.

Head 26 includes a semispherical surface 42 defined about central axis 44. Bottom face 46 is formed opposite semispherical surface 42 and has a female taper 48 formed therein which is configured to receive adapter 24 along central axis 40. In this regard, female taper 48 is formed eccentrically within head 26 such that a radial offset $r_b$ exists between central axis 40 and central axis 44.

Figure 2:
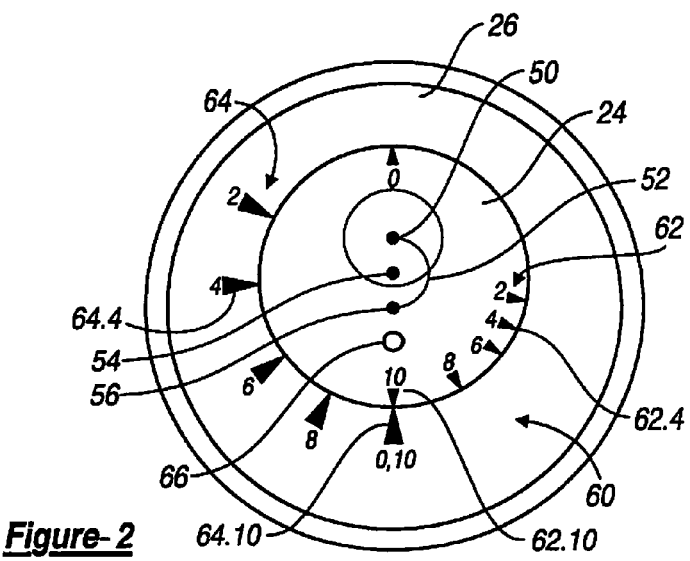
FIG. 2 is a normal view of the adapter and head components of the device illustrated in FIG. 1 shown in an assembled state.

As previously described, the eccentric relationship of central axes 34, 40 and 44 provide an arrangement whereby a relative rotational positioning of adapter 24 with respect to head 26 adjusts the radial offset within a given range. As best seen in FIG. 2, relative positioning of adapter 24 within female taper 48 of head 26 causes centroid 50 defined by female taper 36 to trace a helical path 52 relative to centroid 54 defined by central axis 40. Helical path 62 terminates at centroid 56 defined by central axis 34. A maximum radial offset is achieved when centroid 50 is located directly opposite centroid 56. Similarly, a minimum offset is achieved when centroid 50 aligns with centroid 56. In one example, the maximum radial offset is 10 mm and the minimum radial offset is 0 mm. However, one skilled in the art will recognize that the range of offset may be modified based on the design criteria for a given modular prosthesis system.

With continuing reference to FIG. 2, the shoulder prosthesis 20 is provided with indicia 64 facilitating adjustment and alignment of the radial offset. Specifically indicia 60 includes a first set of indicators 62 formed on adapter 24 and a second set of indicators 64 formed on bottom face 46 of head 26. First and second indicators 62, 64 have a magnitude value associated therewith indicating the amount of radial offset. Furthermore, head indicators 64 include an enlarged arrowhead which indicate the direction of the radial offset. In this manner, indicia 60 provide a radial offset vector which may be utilized to precisely align adapter 24 and head 26 and achieve the desired radial offset.

For example, as shown in FIG. 2, adapter indictor 62.10 associated with a 10 millimeter offset is aligned with head indictor 64.10 associated with 0, 10 offset. Thus, the relative angular position of adapter 24 with respect to head 26 shown in FIG. 2 provides a 10 millimeter offset and the direction of the offset is indicated by arrowhead 64.10. The radial offset may be reduced by removing adapter 24 from head 26, rotating adapter 24 until indicia 60 are properly aligned and inserting adapter 24 into female taper 48 of head 26. For example, an offset of 4 millimeters would be obtained by aligning adapter indictor 62.4 with head indictors 64.4 at which point a 4 millimeter offset in the direction of arrowhead 64.4 would be achieved. In one example, a threaded through bore 66 may be formed in adapter 24 for receiving a threaded member to facilitate a disassembly of adapter 24 from head 26. In certain applications, a removeable plug (not shown) in the form of a bio-compatible cement or the like may be disposed in bore 66 to minimize joint fluid from entering the interface between the adapter 24 and the head 26 through the bore 66.

Figure 3:
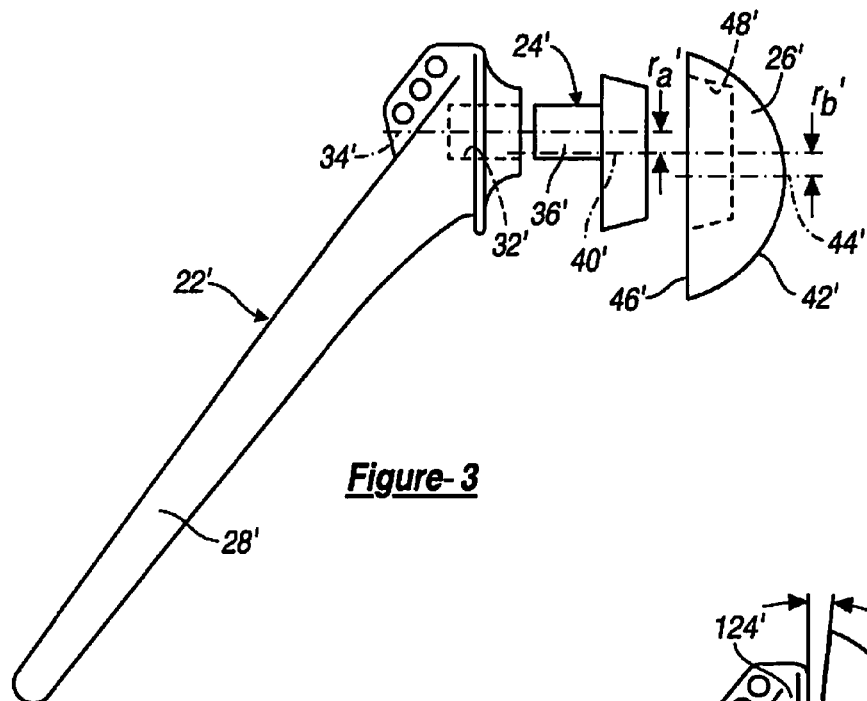
FIG. 3 is an exploded front view of an alternate embodiment of the modular shoulder prosthesis system illustrated in FIG. 1.
Figure 4:
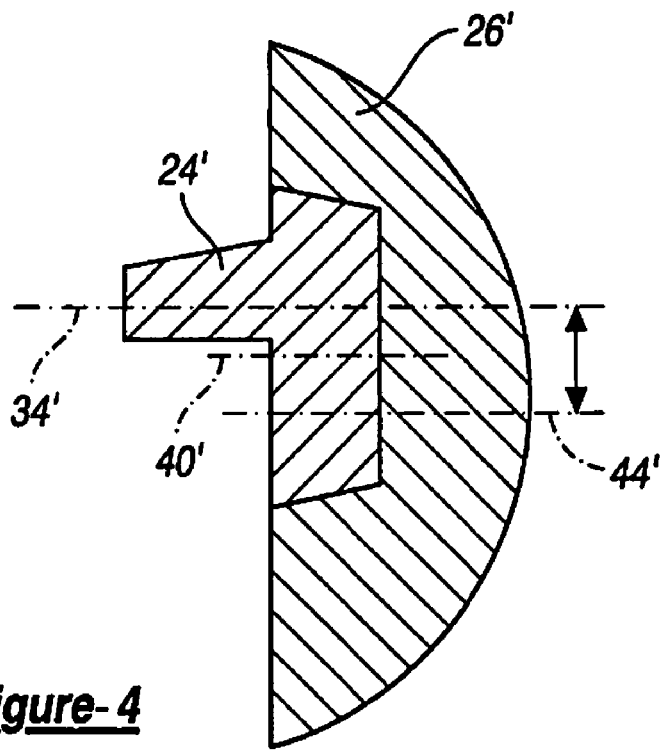
FIG. 4 is a cross-sectional view of the adapter and head shown in FIG. 3 arranged to provide a maximum radial offset.
Figure 5:
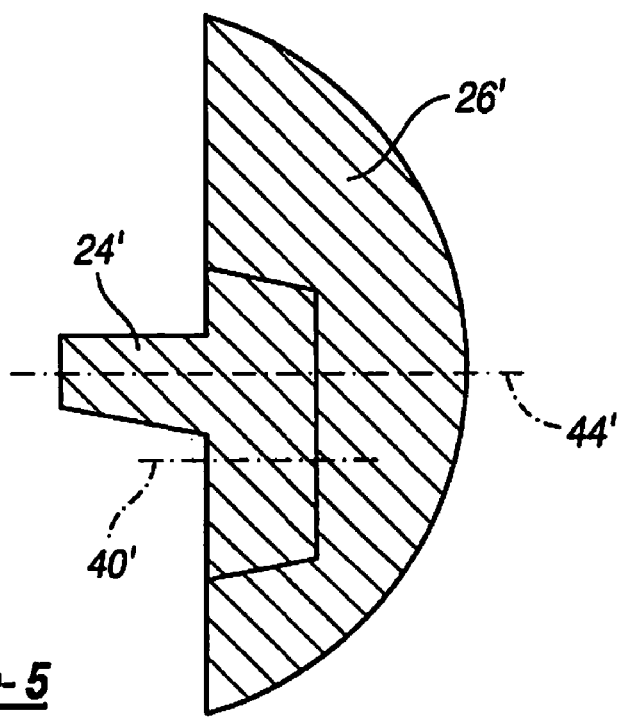
FIG. 5 is a cross-sectional view of the adapter and head shown in FIG. 4 and arranged to provide a minimum radial offset.

With reference now to FIGS. 3 through 5, an alternate embodiment of the present teachings is illustrated in which the adapter has a first male taper adapted to engage the stem and a second male taper adapted to engage the head. With reference now to FIG. 3, stem 22' includes a rod portion 28' and a female taper 32' formed in the end opposite rod 28' which defines central axis 34'. Stem 22' is of the type manufactured and sold by Biomet as a component of its Bio-Modular® Shoulder System. Adapter 24' has a first male taper 36' adapted to be inserted into female taper 32' and a second male taper 38' formed along central axis 40'. Head 26' includes a semispherical surface 42' defined about central axis 44'. Bottom face 46' has a female taper 48' formed therein which is adapted to receive male taper 38' of adapter 24'. Central axis 40' is offset from central axis 34' as indicated at $r_a'$ and central axis 44' is offset from central axis 40' as indicated at $r_b'$. As in the first embodiment, relative rotational positioning of adapter 24' and head 26' provides an adjustable radial offset for shoulder prosthesis 20'.

With reference now to FIG. 4, central axis 34' of male taper 36' is located directly opposite central axis 44' of head 26' to provide a maximum radial offset. With reference now to FIG. 5, head 26' has been rotated 180 degrees relative to adapter 24' such that central axis 44' is collinear with central axis 34'. In this orientation, a minimum radial offset is provided. Indicia similar to that described above with reference to FIG. 2 facilitates alignment of shoulder prosthesis 20'.

Based on the foregoing detailed description, one skilled in the art will readily recognize that one aspect of the present teachings is directed to an adapter and head having eccentric configurations such that a relative rotation therebetween provides an adjustable range of offset configuration.

With reference now to FIGS. 6 through 10, a second alternative embodiment of the present teachings is illustrated which provides for adjustment of the angular inclination between the stem component and the head component in a manner similar to that described with reference to the radial offset. Specially, the shoulder prosthesis system 120 of the second alternative embodiment includes a stem 122, a head 124 having a first angular orientation and an adapter 126 interconnecting the stem 122 and the head 124 such that the adapter 126 has a second angular inclination. The adapter 124 is configured to be rotatably positionable with respect to the head 126 such that the angular inclination of the head 126 relative to the stem 122 may be adjusted.

Figure 6:
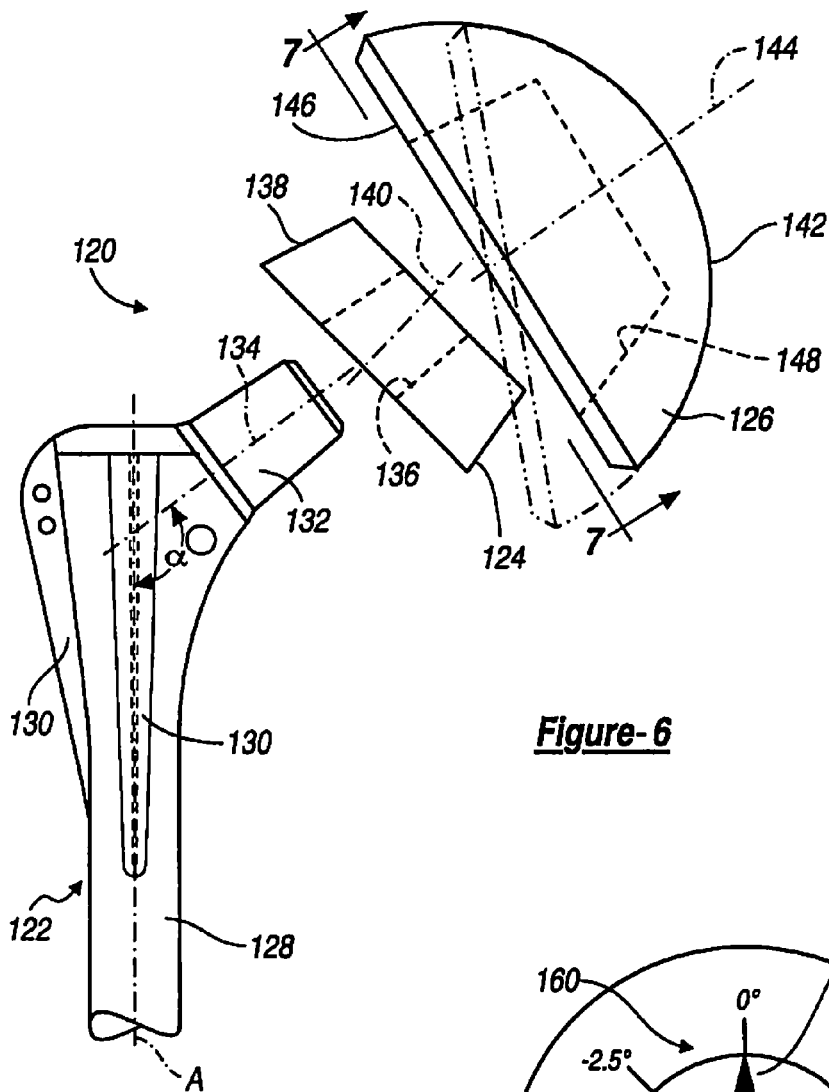
FIG. 6 is an exploded front view of a second alternative embodiment of a modular shoulder prosthesis system according to the present teachings.

With specific reference to FIG. 6, shoulder prosthesis 120 includes stem 122 having rod 128 extending therefrom. A plurality of fins 130 are formed longitudinally along rod 128 parallel to central longitudinal axis A near the upper end of stem 122. A male taper 132 extends from rod 128 at an obtuse angle α with respect to the central longitudinal axis A and defines a central axis 134.

Adapter 124 is a generally cylindrical disc having a female taper 136 formed therein. The outer surface of adapter 124 defines a male taper 138. The central axis 140 of adapter 124 is configured at a first angular orientation with respect to central axis 134. Specifically, central axis 140 is defined by the angle at which female taper 130 is oriented relative to the bottom surface 125 of adapter 124. In one example, central axis 140 is disposed at a +5 degree angular inclination with respect to central axis 134.

Head 126 includes a semispherical surface 142 and a flat bottom face 146 having a female taper 148 formed therein. Female taper 148 defines central axis 144 which is disposed at an angular inclination relative to a central axis 140. Specifically, central axis 144 is defined by the angle at which female taper 144 is oriented relative to bottom face 146. In one example, central axis 144 is disposed at a −5 degree angular inclination with respect to central axis 140.

The relative rotational position of adapter 124 with respect to the head 126 defines the adjustment to the prosthesis inclination relative to central axis 34. For example, as illustrated in FIG. 6, adapter 126 provides a +5 degree inclination which is canceled by the −5 inclination provided in head 126. Thus, when adapter 124 and head 126 are assembled a net zero angular inclination is achieved. An angular adjustment may be provided by rotating adapter 124 relative to head 126 such that a net angular inclination is provided. For example, when adapter 124 is rotated clockwise 90 degrees, the angular inclination of central axis 140 combines with the angular inclination of central axis 144 to provide a +5 degree angular inclination of head 126 relative to central axis 134. Likewise, an additional 90 degree rotation of adapter 124 will provide an overall adjustment of +10 degrees in the angular inclination. In one example, a range of angular inclination is provided between 0° and 10°. However, one skilled in the art will recognize that the range of angular inclination may be modified based on the design criteria for a given modular prosthesis system.

Figure 7:
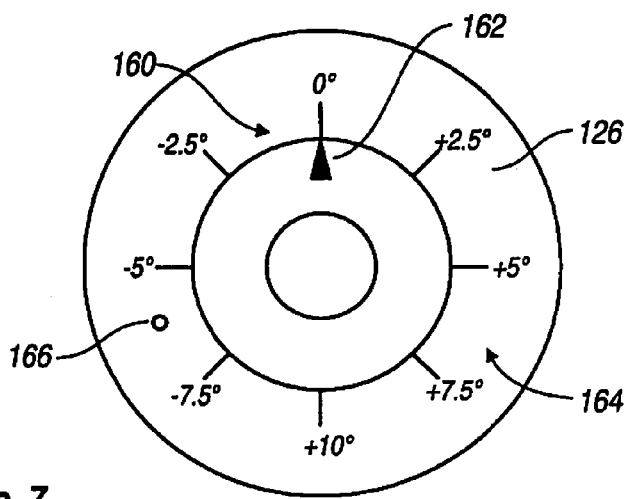
FIG. 7 is a normal view of the adapter and head illustrated in FIG. 6 shown in an assembled state.

With continuing reference to FIG. 7, adapter 124 and head 126 are provided with inclination indicia 160 which facilitates identification of the magnitude and direction of the angular inclination provided by shoulder prosthesis system 120. Specifically, angular indicia 160 includes a first indictor 162 on adapter 124 and a plurality of second indicators 164 provided on bottom face 146 of head 126. Adapter indicator 162 is an arrowhead which indicates the direction of the angular inclination. Head indicators 164 provide a magnitude of angular inclination as well as an alignment mark which cooperates with adapter indictor 162 to provide the angular inclination vector (i.e. magnitude and direction).

Figure 8:
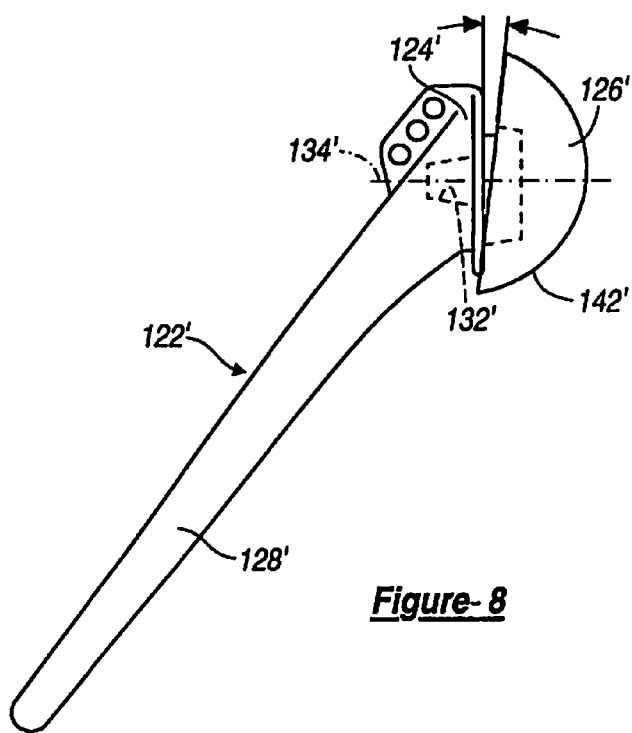
FIG. 8 is an alternate embodiment of the modular shoulder prosthesis system illustrated in FIG. 6.
Figure 9:
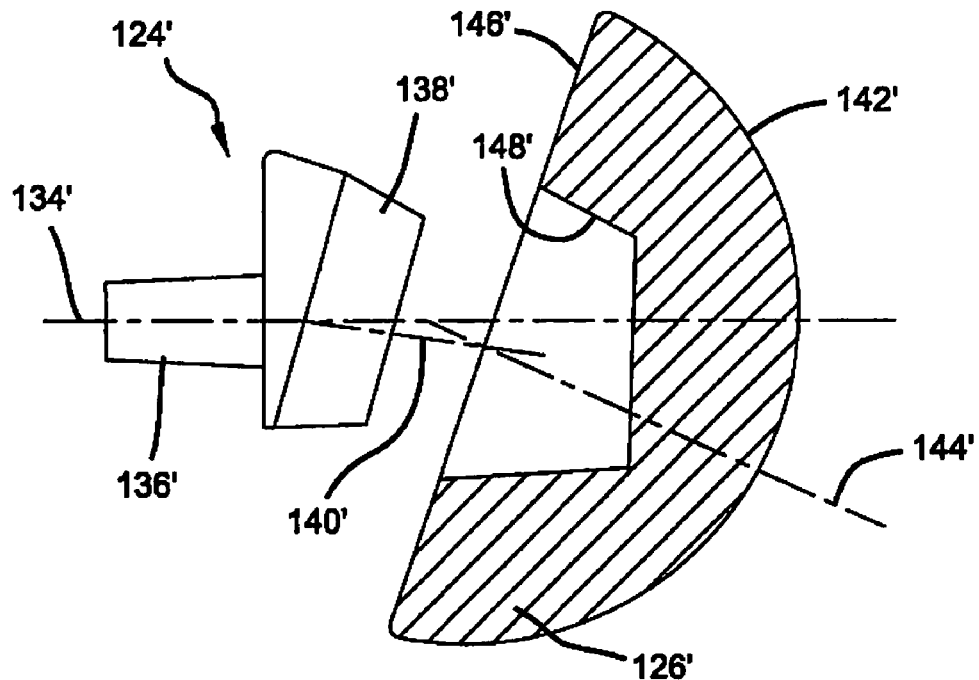
FIG. 9 is a partial cross-sectional view showing the adapter and head of FIG. 8 arranged to provide a maximum angular inclination.
Figure 10:
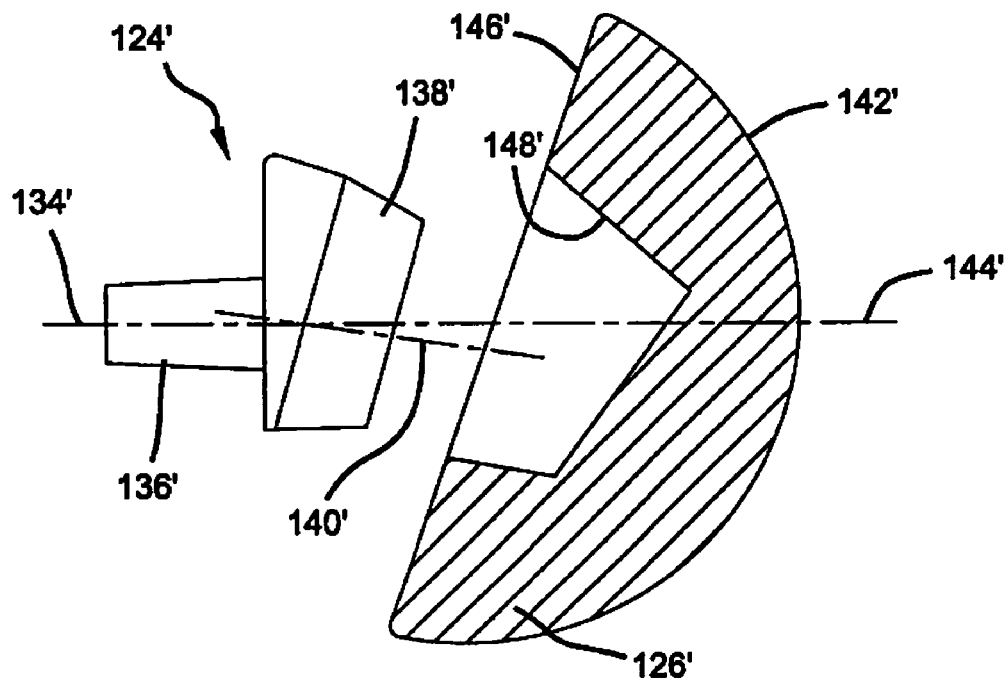
FIG. 10 is an illustration of the adapter and head similar to that shown in FIG. 9 and arranged to provide a minimum angular inclination.

With reference now to FIGS. 8 through 10, an alternate embodiment to the second alternative embodiment is illustrated in which the adapter has a first male taper adapted to engage the stem and a second male taper adapted to engage the head. With reference now to FIG. 8, stem 122' includes a rod portion 128' and a female taper 132' formed in the end opposite rod 128' which defines central axis 134'. Adapter 124' has a first male taper 136' adapted to be inserted into female taper 132' and a second male taper 138' formed along central axis 140'. Head 126' includes a semispherical surface 142' defined about central axis 144'. Bottom face 146' has a female taper 148' formed therein which is adapted to receive male taper 138' of adapter 124'. Central axis 140' is angularly inclined relative to central axis 34' and central axis 144' is angularly inclined relative to central axis 140'. Relative rotational positioning of adapter 124' and head 126' provides an adjustable angular inclination for shoulder prosthesis 120'.

With reference now to FIG. 9, the angular inclination of central axis 134' of male taper 136' is complementary with the central axis 144' of head 26' to provide a maximum angular inclination. With reference now to FIG. 10, head 126' has been rotated 180 degrees relative to adapter 124' such that the angular inclination of central axis 144' is opposing central axis 134' to provide a minimum angular inclination.

From the foregoing description of various embodiments, one skilled in the art will readily recognize that the present teachings are directed to a modular shoulder prosthesis in which the radial offset and/or the angular inclination (i.e. inversion and retroversion) of the head relative to the stem may be adjusted by relative rotational positioning of an adapter interdisposed between the stem and head components of the shoulder prosthesis. In this way, a range of radial offsets and/or angular inclinations may be provided without requiring numerous additional components. The various embodiments have discussed a radial offset adjustment or an angular inclination adjustment independently; however, one skilled in the art will readily recognize that a shoulder prosthesis system may incorporate both aspects of a radial and angular adjustment. Where a single adapter utilized to interconnect the stem and the head, an interrelationship exists between the radially offset adjustment and the angular inclination adjustment. In combination, a system could be employed which utilized two intermediate adapters such that the radial offset and angular inclination adjustment are isolated and thus independent. For example, the interface between a first adapter and a second adapter would provide the desired radial adjustment as described in particular reference to the first embodiment and the interface between the second adapter and the head would provide the angular inclination as described with reference to the second alternative embodiment. In such a system, each of the radial offset and angular inclination adjustments would be provided by a single interface, thereby minimizing the interrelation between both adjustments resulting from a single intermediate adapter.

Figure 11:
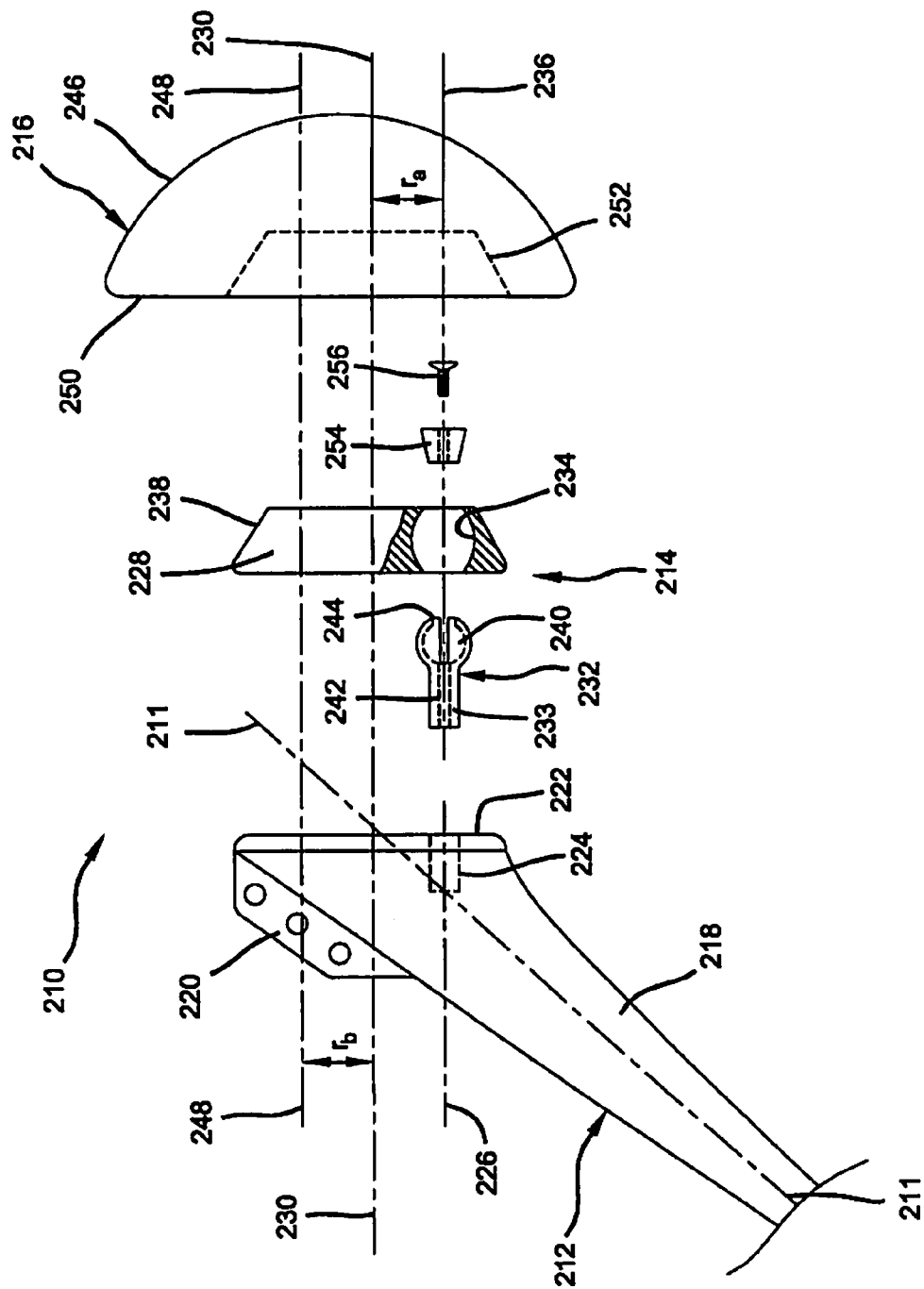
FIG. 11 is an exploded front view of a third alternative embodiment of a modular shoulder prosthesis system according to the present teachings.
Figure 12:
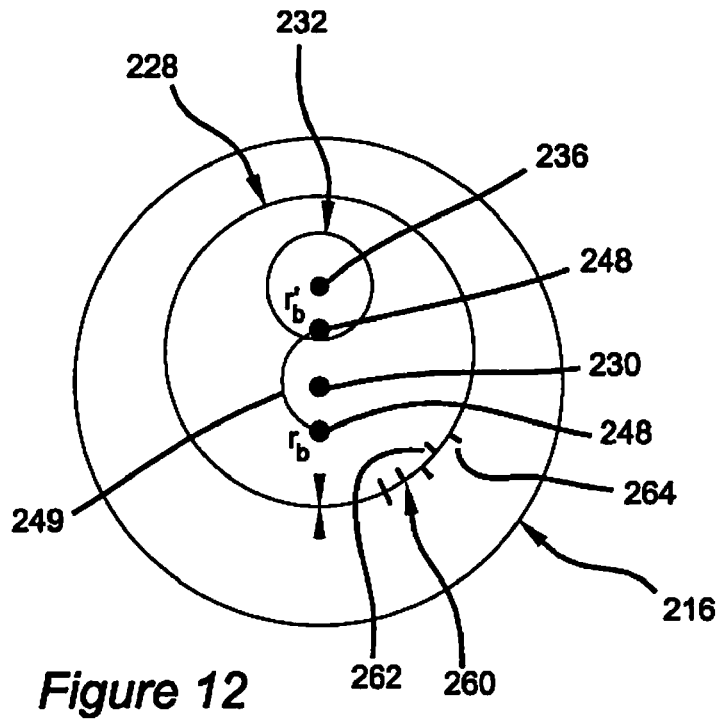
FIG. 12 is a normal view of the adaptor and head components of the device shown in FIG. 11 oriented in a first position.
Figure 13:
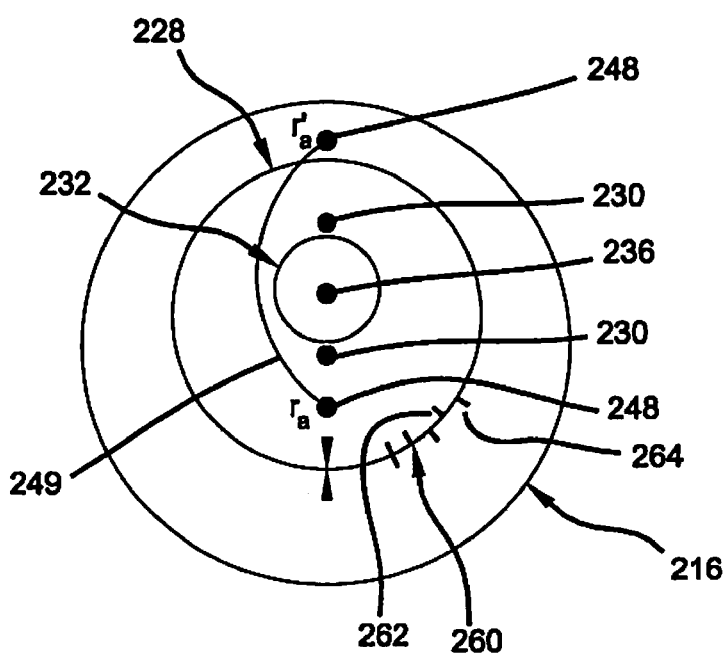
FIG. 13 is a normal view similar to FIG. 12 with the components oriented in a second position.

With reference now to FIGS. 11-13, a third alternative embodiment of the present teachings is illustrated which provides for adjustment of both the radial offset and the angular inclination. Specifically, the shoulder prosthesis 210 is provided and includes a stem 212, an adaptor 214 and a head 216. The stem 212 includes a longitudinal axis A along its length and further includes a rod portion 218 adapted to be received into the medullary canal of the humerus. A plurality of fins 220 are formed near the proximal end of the rod 218 for locating and fixing the stem 212 within the humerus whereby the proximal end of the rod 218 has a substantially larger body than that of the distal end and includes a proximal face 222 having a bore 224 formed therein along a central axis 226 for receiving the adaptor 214. The proximal face 222 extends from the stem 212 along axis 226 and provides a location for interconnecting the stem 212 with the adaptor 214. Further, the proximal face 222 provides sufficient clearance for angular and radial adjustments of the adaptor 214 and the head 216 as will be discussed in more detail below.

The adaptor 214 is a generally cylindrical member including an outer ring 228 having a central axis 230 and a ball stud 232 rotatably connected to the ring 228. The ring 228 includes an attachment aperture 234 having a central axis 236 formed therethrough for rotatable engagement with the ball stud 232. The ring 228 further includes an outer surface having a male taper 238 for engagement with the head 216.

The ball stud 232 includes a shank segment 233 for engagement with the bore 224 of the stem 212 and a divided ball segment 240 for attachment to attachment aperture 234 of the ring 228. The ball stud 232 further includes a second bore 242 formed therein for interaction with a fastener 244 for selectively securing the ring 228 to the ball stud 232 in a fixed orientation. Fastener 244 includes a wedge portion 254 and a set screw 256 as best shown in FIG. 11. Set screw 256 is received by a central bore of the wedge 254, whereby as the set screw 256 is driven into the wedge 254, the wedge 254 expands within the attachment aperture 234 of the ring 228 thereby securing the ring 228 and ball stud 232 in a fixed relationship. In this regard, the central axis 236 of the ball stud 232 is concentric with central axis 226 of the proximal face 222 and is received by the attachment aperture 234 such that the central axis 236 of the ball stud 232 is eccentric to the central axis 230 of the ring 228 as indicated by $r_a$.

The head 216 is rotatably supported by the adaptor 214 and includes a semispherical surface 246 defined about a central axis 248 adapted for mating engagement with the glenoid cavity of a scapula. The head 216 further includes a bottom surface 250 formed opposite the semispherical surface 246 having a female taper 252 for mating engagement with the male taper 238 of the ring 228. In this regard, the female taper 252 is received eccentrically within the head 216 such that a radial offset $r_b$ exists between the central axis 230 of the ring 228 and the central axis 248 of the head 216. While the present teachings disclose a head 216 for mating engagement with the glenoid cavity of a scapula, it is anticipated that the head 216 could also be received by a prosthetic device replacing a severely damaged glenoid cavity and should be considered within the scope of the present teachings.

As previously described, the eccentric relationship of the central axes 230, 236 and 248 provides an arrangement whereby a relative rotational positioning of the adaptor 214 with respect to the head 216 or a relative rotational positioning of the adaptor 214 with respect to the ball stud 232 or a combination thereof adjusts the radial offset of the head 216 relative to the longitudinal axis A of the stem 212.

With particular reference to FIG. 13, relative positioning of the head 216 to the longitudinal axis A of the stem 212 is accomplished by a first radial adjustment method. In the first radial adjustment method, the relative positioning of the ring 228 within the female taper 252 of the head 216 causes the central axis 248 of the head 216 to be rotated relative to the central axis 230 of the ring 228. The radial offset between the central axis 248 and the central axis 230 is again denoted by $r_b$ at its minimum and by $r_b'$ at its maximum value. FIG. 2 further traces the movement of axis 248 from $r_b$ to $r_b'$ as indicated by path 249, while each position along path 249 signifies a potential adjustment of the head 216 relative to the longitudinal axis A of the stem 212.

With particular reference to FIGS. 12 and 13, relative positioning of the head 216 to the longitudinal axis A of the stem 212 is accomplished by a second radial adjustment method. In the second radial adjustment method, the relative positioning of the central axis 230 of the ring 228 and the central axis 236 of the ball stud 232 causes the central axis 248 of the head 216 to be rotated. Again, $r_a$ is used to designate the minimum offset between the central axis 230 of the ring 228 and the central axis 236 of the ball stud 232 while $r_a'$ is used to designate the maximum offset. FIG. 3 further traces the movement of axis 248 from $r_a$ to $r_a'$ as indicated by path 251, while each position along path 251 signifies a potential adjustment of the head 216 relative to the longitudinal axis A of the stem 212. For discussion purposes, the head 216 does not rotate relative to the ring 228 when making an adjustment of the ball stud 232 relative to the ring 228, but it should be understood that both adjustment methods could be used concurrently to achieve an overall desired radial offset of the head 216 relative to the longitudinal axis A of the stem 212.

In addition to providing a radial offset, the shoulder prosthesis 210 further provides an angular adjustment of the head 216 relative to the longitudinal axis A of the stem 212 for both inversion and retroversion adjustments. As best shown in FIG. 3, the central axis 248 of the head 216 rotates about the central axis 236 of the ball stud 232, which is concentric with the central axis 226 of the first bore 224. As previously discussed, the divided ball segment 240 of the ball stud 232 rotatably supports the ring 228 while the ring 228 supports the head 216. By articulating either the head 216 or the ring 228, the ring 228 will rotate on the divided ball segment 240 of the ball stud 232, thereby providing the head 216 with an angular adjustment relative to the longitudinal axis A of the stem 212. For discussion purposes, the first and second radial adjustment methods are not utilized while making an angular adjustment of the head 216, however, it should be understood that both adjustment methods may be used concurrently with the angular adjustment method and with one another to achieve an overall desired angular and radial relationship of the head 216 relative to the longitudinal axis A of the stem 212.

With continuing reference to FIGS. 2 and 3, the shoulder prosthesis is provided with indicia 260 facilitating adjustment and alignment of the radial offset. Specifically, indicia 260 includes a first set of indicators 262 formed on the ring 228 and a second set of indicators 264 formed on the bottom face 250 of the head 216. First and second indicators 262, 264 have a magnitude value associated therewith indicating the amount of radial offset. Furthermore, the head indicators 264 include an enlarged arrowhead which indicates the direction of the radial offset. In this manner, indicia 260 provide a radial offset vector which may be utilized to precisely align the adaptor 214 and the head 216 and achieve the desired radial offset.

In reference to all of the above-described embodiments, various tapered surfaces have been referenced at interfaces between the stem, adapter and head. In one example, these tapered surfaces are configured as morse-type tapers which provide a self locking interface. While morse-type tapers are described herein, one skilled in the art will readily recognize that other means may be incorporated for providing a locking interface between the various components of the shoulder prosthesis system. In this regard, one or more interfaces may be interlocked with the use of an additional fastener to insure locking engagement therebetween.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A shoulder prosthesis comprising:
a stem having a first longitudinal axis;
an adaptor having a first portion including a first taper having a first taper axis of symmetry and a first diameter and a second portion positioned adjacent to the first portion and including a second taper having a second taper axis of symmetry and a second diameter, the first taper axis offset from and parallel to the second taper axis, the second diameter smaller than the first diameter, the first taper formed along the first diameter and the second taper formed along the second diameter;
a plurality of indicia associated with the adaptor; and
a head rotatably supported by the adaptor, the head having a semi-spherical articulating surface, and a third axis of symmetry of the head offset from and substantially parallel to the first taper axis and the second taper axis,
wherein the head is coupled to the first taper and is positionable relative to the stem through rotation of the adaptor about the first taper axis for adjusting a radial offset of the head relative to the longitudinal axis of the stem and the plurality of indicia indicate an alignment of the radial offset.

2. The shoulder prosthesis of claim 1, wherein the first taper further comprises a first male taper.

3. The shoulder prosthesis of claim 1, wherein the semispherical articulating surface is a generally hemispherical outer surface adapted for mating engagement with a glenoid cavity of a scapula and a bottom surface of the head defines a female taper formed therein.

4. The shoulder prosthesis of claim 3, wherein the female taper rotatably receives the first taper of the adaptor.

5. The shoulder prosthesis of claim 1, wherein the stem further comprises a tapered portion, and the tapered portion rotatably receives the adaptor.

6. The shoulder prosthesis of claim 1, wherein the stem further comprises a proximal face having a bore, and the second portion is receivable within the bore of the proximal face to enable the rotation of the adaptor about the second taper axis.

7. A shoulder prosthesis comprising:
a stem having a longitudinal axis and a proximal face, the proximal face defining a bore;
an adaptor having a first portion directly adjacent to a second portion, at least a portion of the first portion received within the bore of the stem to couple the adaptor to the stem, the first portion having a first diameter and a second taper formed along the first diameter having a second taper axis of symmetry, the second portion having a second diameter different than the first diameter and the second portion defining a first taper formed along the second diameter having a first taper axis of symmetry, the first taper axis offset from and parallel to the second taper axis, the adaptor including a plurality of indicia; and
a head having a bottom face opposite a semispherical articulating surface, the bottom face having a third taper that mates with the first taper of the second portion to couple the head to the adaptor, the head having a third axis of symmetry of the head offset from and substantially parallel to the first taper axis and the second taper axis,
wherein the rotation of the adaptor relative to the stem adjusts a radial offset of the head relative to the longitudinal axis of the stem and the plurality of indicia on the adaptor indicate an alignment of the radial offset.

8. The shoulder prosthesis of claim 7, wherein the second diameter is greater than the first diameter.

9. The shoulder prosthesis of claim 8, wherein the adaptor further comprises a one-piece adaptor.

10. A shoulder prosthesis comprising:
a stem having a longitudinal axis and a proximal face, the proximal face defining a bore;
an adaptor having a first portion opposite a second portion, the first portion wholly received within the bore of the stem to couple the adaptor to the stem, the first portion having a first diameter and positioned about a first axis, the second portion having a second diameter different than the first diameter, the second portion defining a first taper and positioned about a second axis, the second axis offset from and substantially parallel to the first axis, the adaptor including a plurality of indicia; and
a head having a semispherical articulating surface and a bottom face opposite the semispherical articulating surface, the head having a third axis of symmetry of the head offset from and substantially parallel to the first axis and the second axis, the bottom face having a second taper that mates with the first taper of the second portion so that the second portion is wholly received within the head to couple the head to the adaptor,
wherein the rotation of the adaptor relative to the stem adjusts the radial offset of the head relative to the longitudinal axis of the stem and the plurality of indicia on the adaptor indicate an alignment of the radial offset.

11. The shoulder prosthesis of claim 10, wherein the adaptor further comprises a one-piece adaptor.

12. The shoulder prosthesis of claim 10, wherein the first taper is a male taper and the second taper is a female taper.

* * * * *

UNITED STATES PATENT AND TRADEMARK OFFICE
CERTIFICATE OF CORRECTION

| | | |
|---|---|---|
| PATENT NO. | : 8,236,059 B2 | Page 1 of 1 |
| APPLICATION NO. | : 12/911238 | |
| DATED | : August 7, 2012 | |
| INVENTOR(S) | : Kevin T. Stone et al. | |

It is certified that error appears in the above-identified patent and that said Letters Patent is hereby corrected as shown below:

<u>Title Page, Item (54) and Column 1, Line 1, Title,</u>
Replace "SHOULDER PROTHESIS" with --SHOULDER PROSTHESIS--

<u>Column 2,</u>
Line 67, replace "adjusted" with --adjustment--

Signed and Sealed this
Twentieth Day of November, 2012

David J. Kappos
*Director of the United States Patent and Trademark Office*